US 6,527,803 B1

(12) United States Patent
Crozet et al.

(10) Patent No.: US 6,527,803 B1
(45) Date of Patent: Mar. 4, 2003

(54) INTERSOMATIC SPINE IMPLANT HAVING ANCHORING ELEMENTS

(75) Inventors: Yves Crozet, Seynod (FR); Régis Le Couedic, Cestas (FR); Fabien Gauchet, route de Rocquemont (FR); Denis Pasquet, Bordeaux (FR)

(73) Assignee: Dimso (Distribution Medicale Du Sud-Ouest) (FR)

( * ) Notice: Subject to any disclaimer, the term of this patent is extended or adjusted under 35 U.S.C. 154(b) by 0 days.

(21) Appl. No.: 09/720,150

(22) PCT Filed: Jun. 22, 1999

(86) PCT No.: PCT/FR99/01492

§ 371 (c)(1),
(2), (4) Date: Dec. 21, 2000

(87) PCT Pub. No.: WO99/66867

PCT Pub. Date: Dec. 29, 1999

(30) Foreign Application Priority Data

Jun. 23, 1998 (FR) .............................................. 98 07909
Jun. 17, 1999 (FR) .............................................. 99 07669

(51) Int. Cl.[7] .................................................. A61F 2/44
(52) U.S. Cl. .............................. 623/17.11; 623/17.16; 606/31
(58) Field of Search ........................... 623/17.11, 17.16; 606/61, 62, 63

(56) References Cited

U.S. PATENT DOCUMENTS

| 5,458,641 | A | * | 10/1995 | Ramirez Jimenez | ......... 623/17 |
| 5,554,191 | A | * | 9/1996 | Lahille | ..................... 623/17.11 |
| 5,653,763 | A | * | 8/1997 | Errico | ..................... 623/17.11 |
| 5,658,335 | A | * | 8/1997 | Allen | ..................... 623/17.11 |
| 5,702,391 | A | | 12/1997 | Lin | ................................ 606/61 |
| 5,800,547 | A | * | 9/1998 | Schafer | ..................... 623/17.11 |
| 5,800,550 | A | * | 9/1998 | Sertich | ..................... 623/17.11 |
| 6,102,950 | A | * | 8/2000 | Vaccaro | ..................... 623/17.11 |
| 6,129,763 | A | * | 10/2000 | Chauvin | ..................... 623/17.11 |
| 6,176,882 | B1 | * | 1/2001 | Biedermann | ............. 623/17.11 |
| 6,179,873 | B1 | * | 6/2001 | Zientek | ..................... 623/17.11 |

FOREIGN PATENT DOCUMENTS

| EP | 0 260 044 A1 | 3/1988 |
| EP | 0 637 439 A1 | 2/1995 |
| EP | 0 697 200 A1 | 2/1996 |
| FR | 2 717 068 A1 | 9/1995 |
| FR | 2 727 003 A1 | 5/1996 |
| WO | 97/06753 | 2/1997 |
| WO | 97/48352 | 12/1997 |

OTHER PUBLICATIONS

The Wordsworth Dictionary of Science and Technology, W&R Chambers Ltd and Cambridge University Press (1988), p. 128.*

* cited by examiner

Primary Examiner—Paul B. Prebilic
(74) Attorney, Agent, or Firm—Lerner, David, Littenberg, Krumholz & Mentlik, LLP

(57) ABSTRACT

The intersomatic spine implant comprises a body, at least one anchoring element movable relative to the body to project from a contact face of the body making contact with a vertebra, and at least one cam slidable relative to the body and suitable for displacing the anchoring element relative to the body by the effect of a ramp engaging the anchoring element. The cam and the anchoring element are arranged so that the cam moves the anchoring element in two opposite displacement directions.

21 Claims, 10 Drawing Sheets

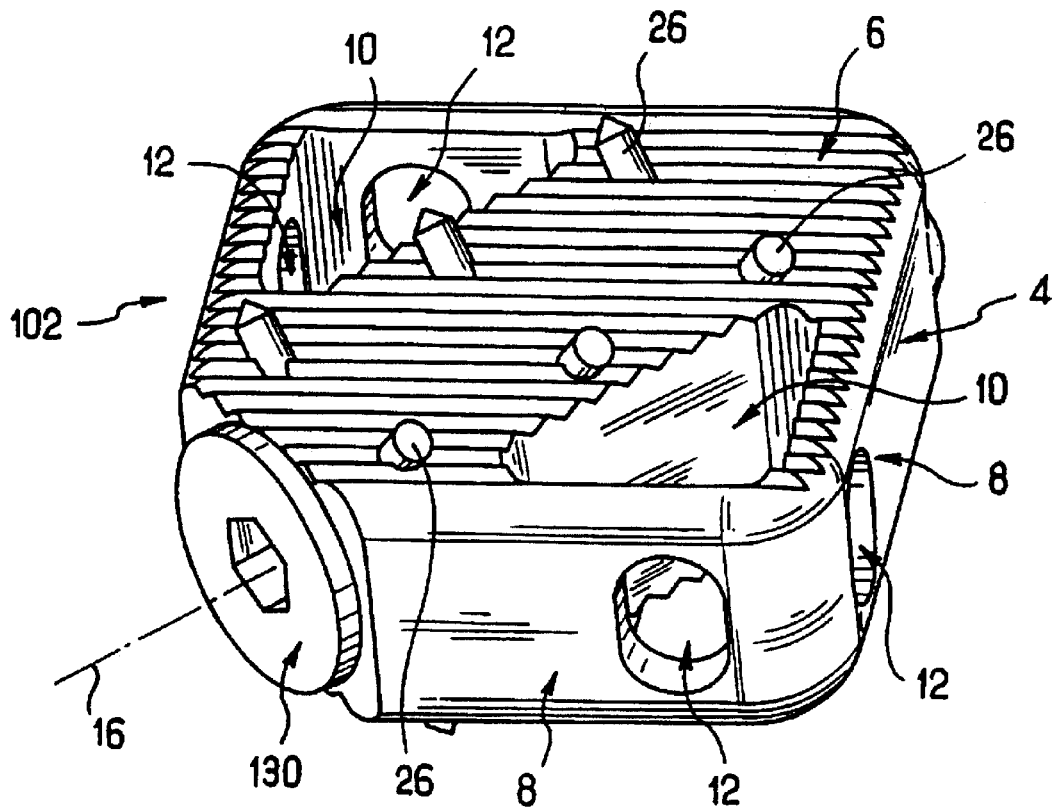
FIG_1
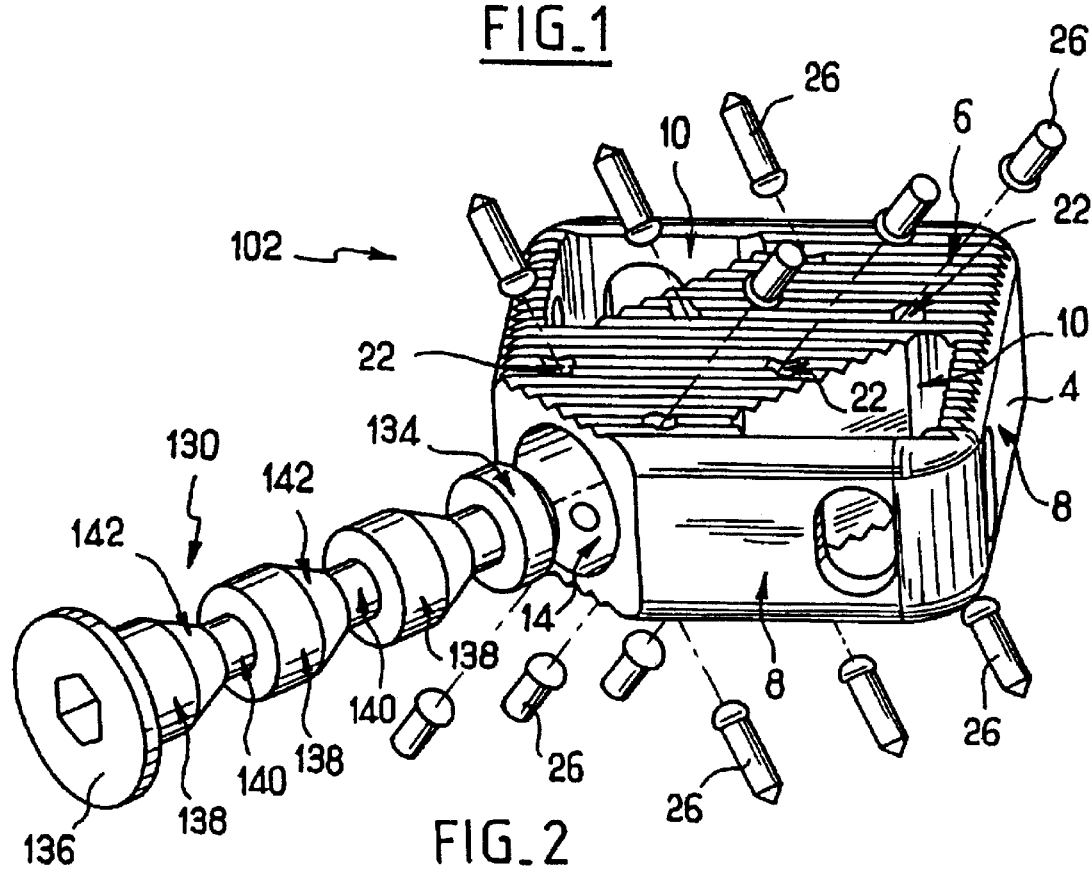
FIG_2

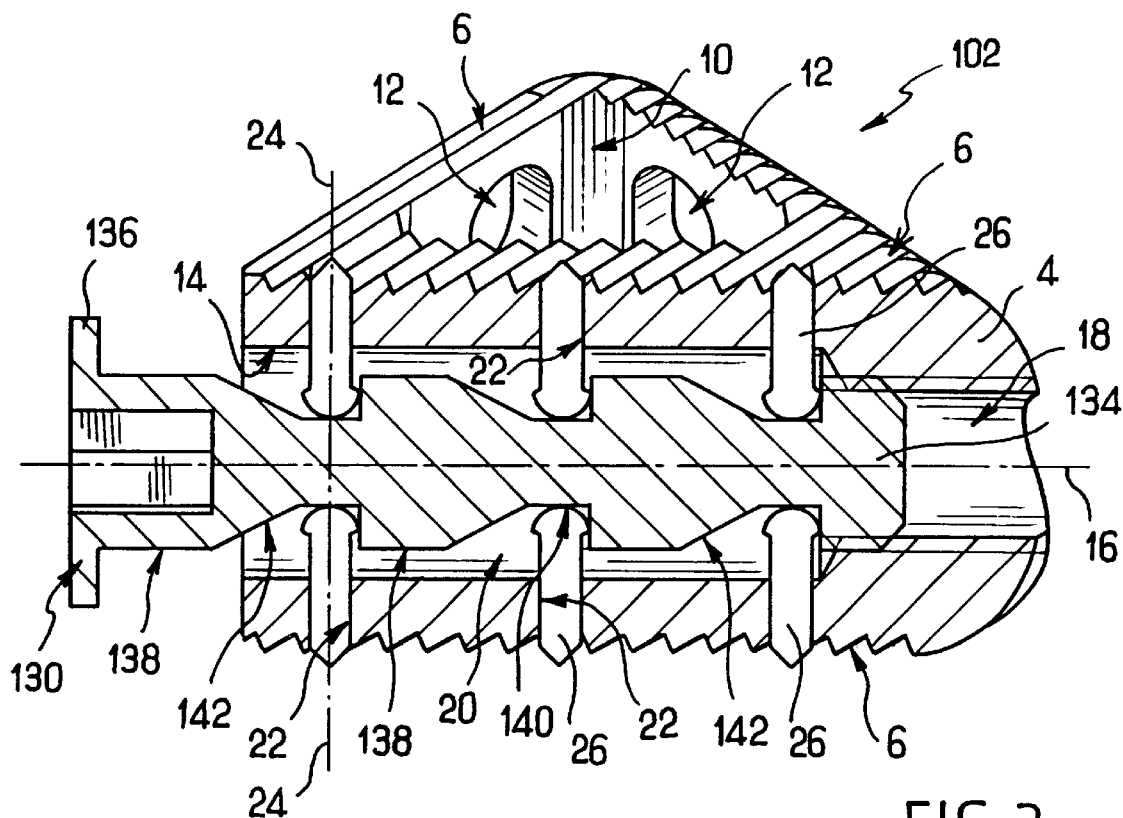
FIG_3
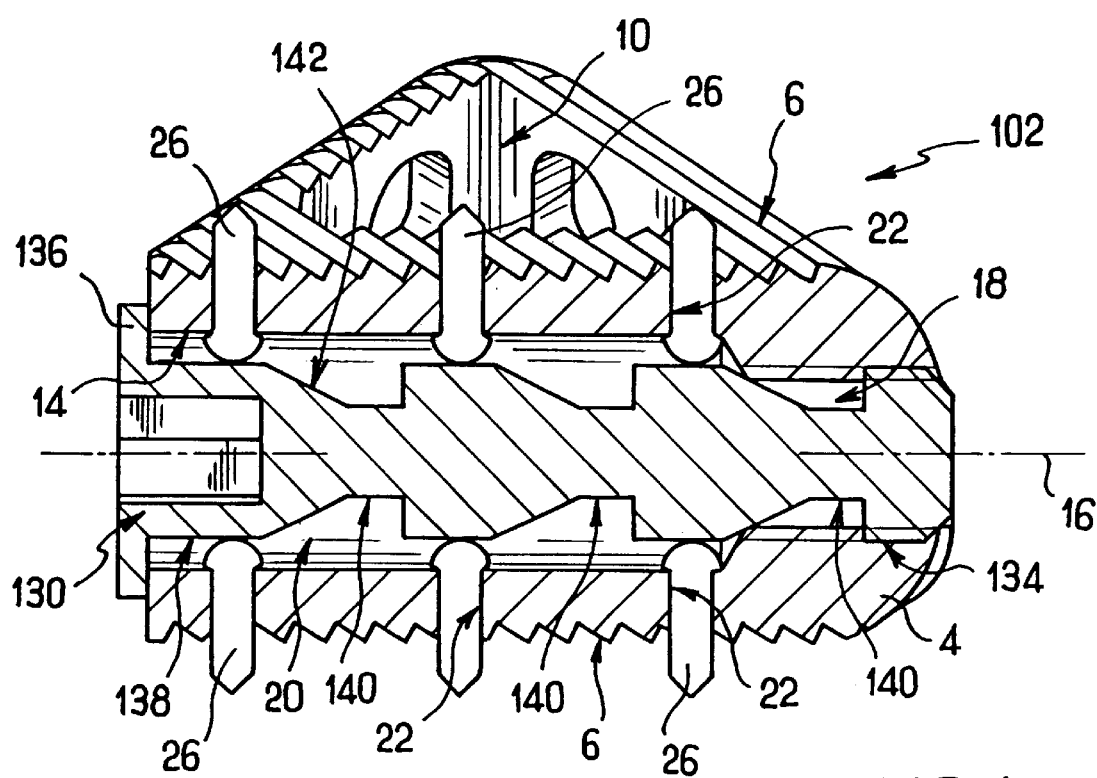
FIG_4

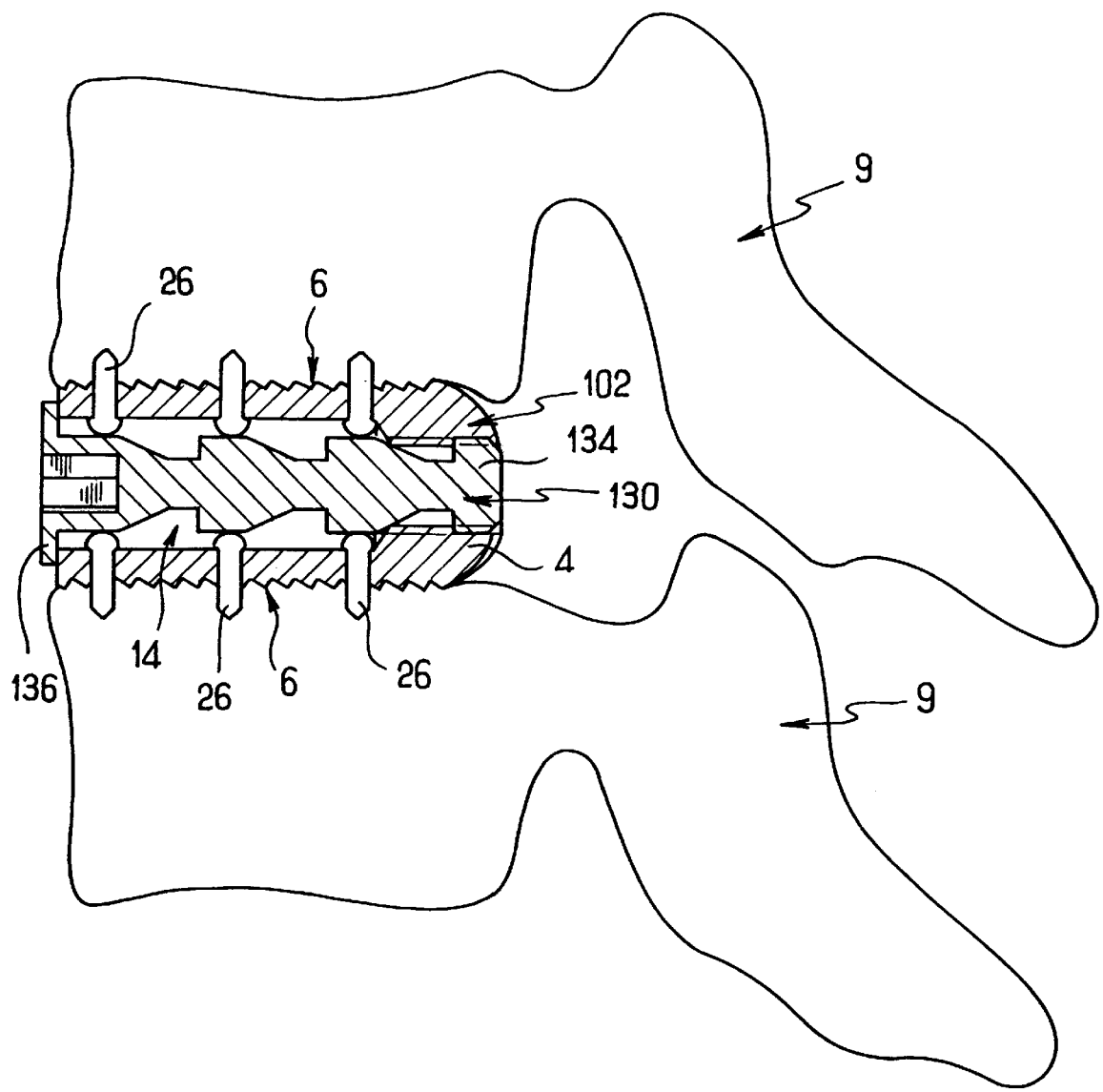
FIG_5

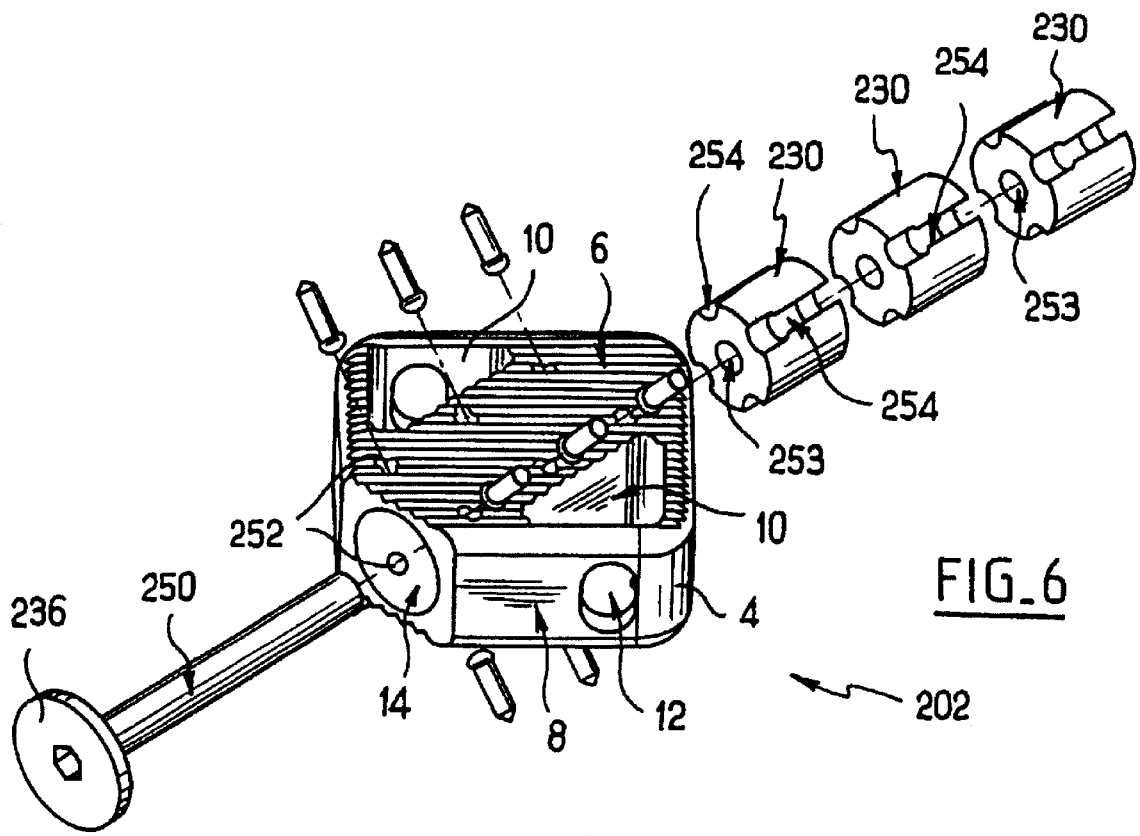
FIG_6
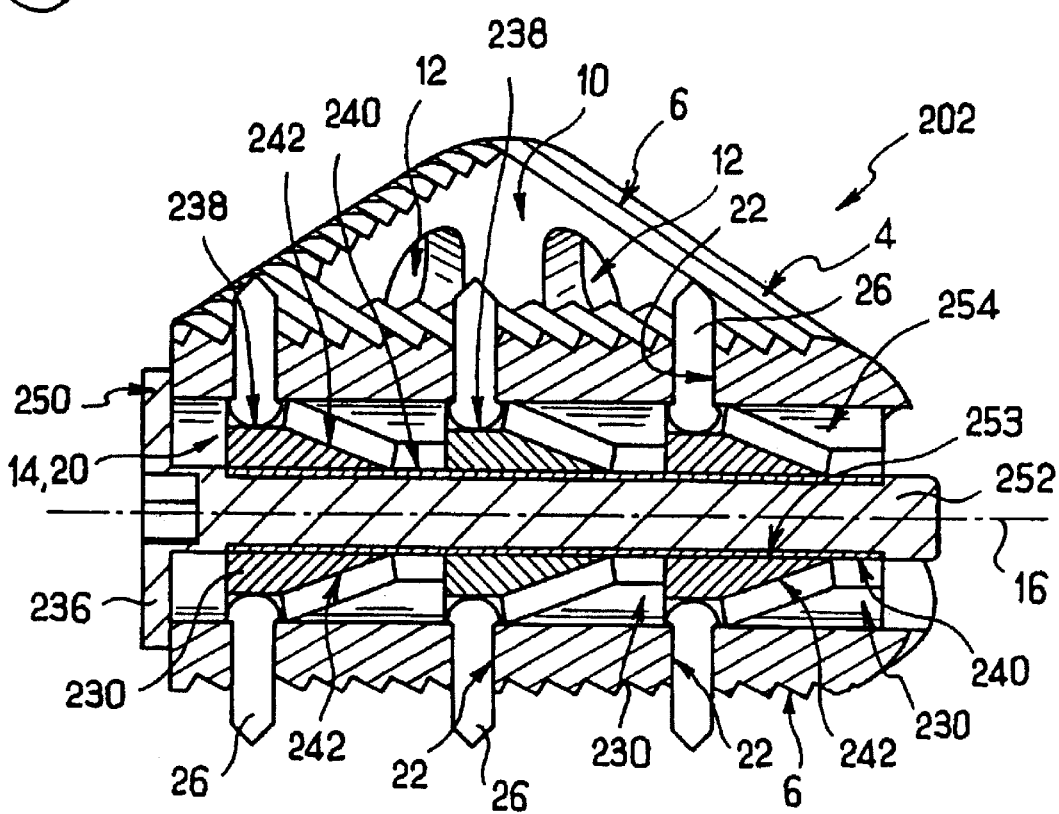
FIG_7

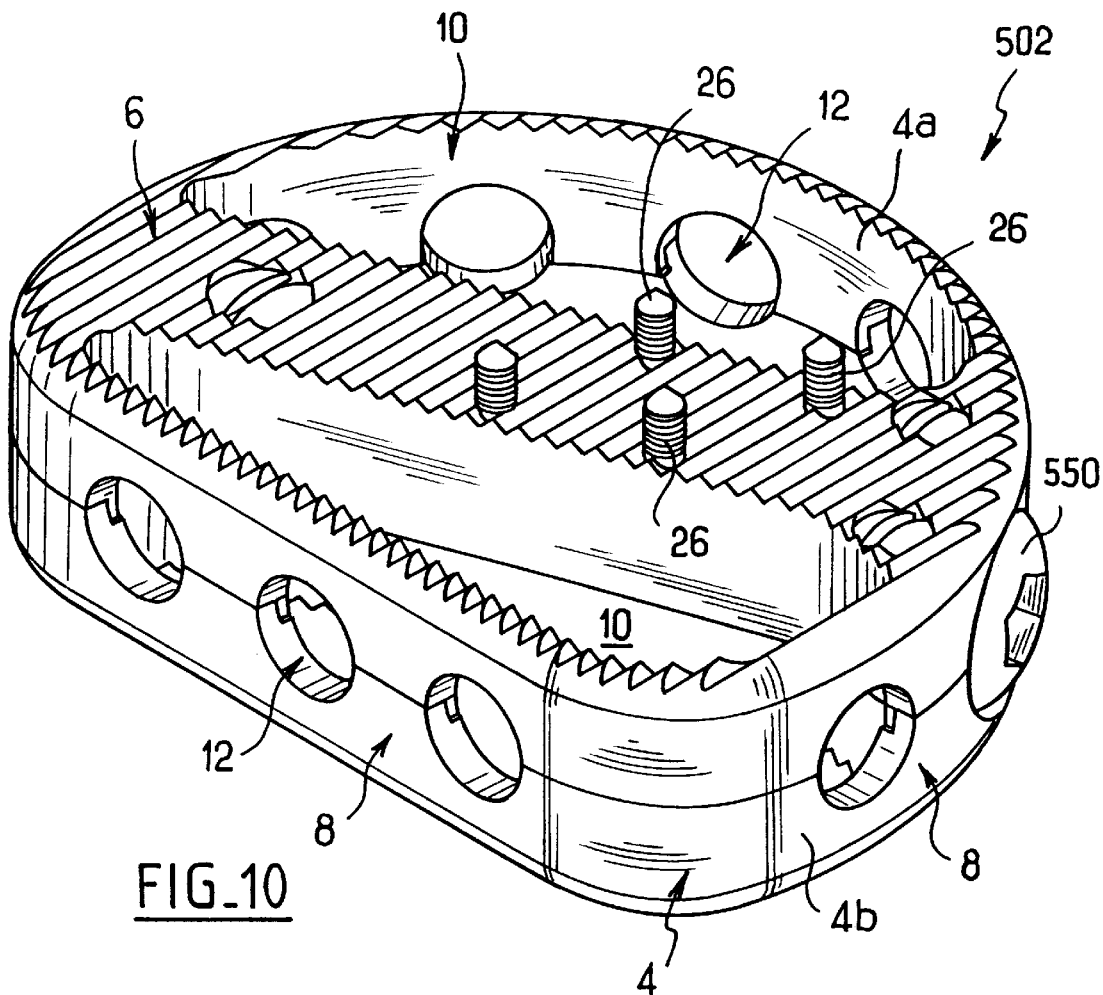
FIG_10
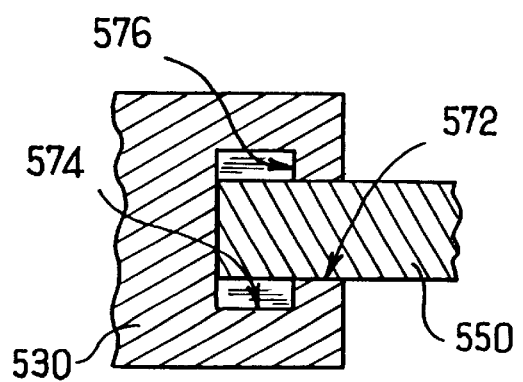
FIG_12

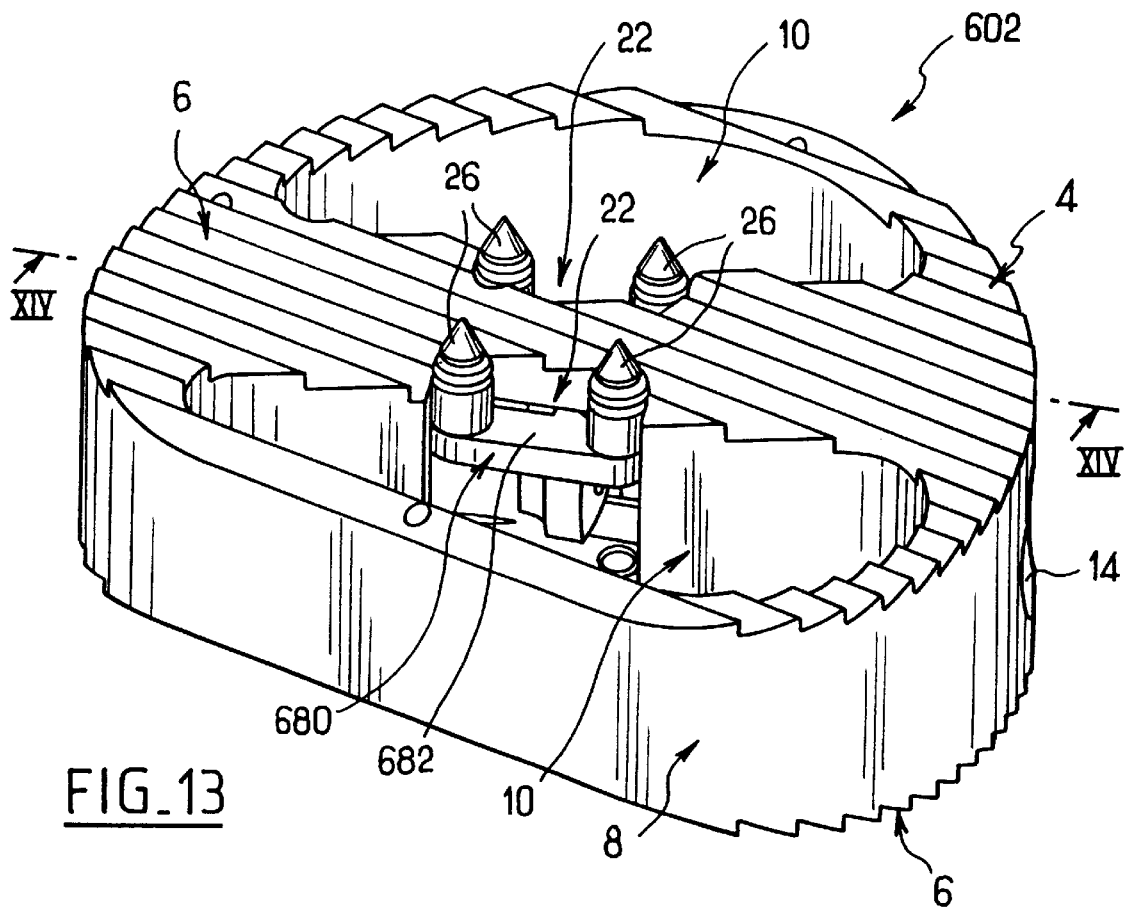
FIG_13
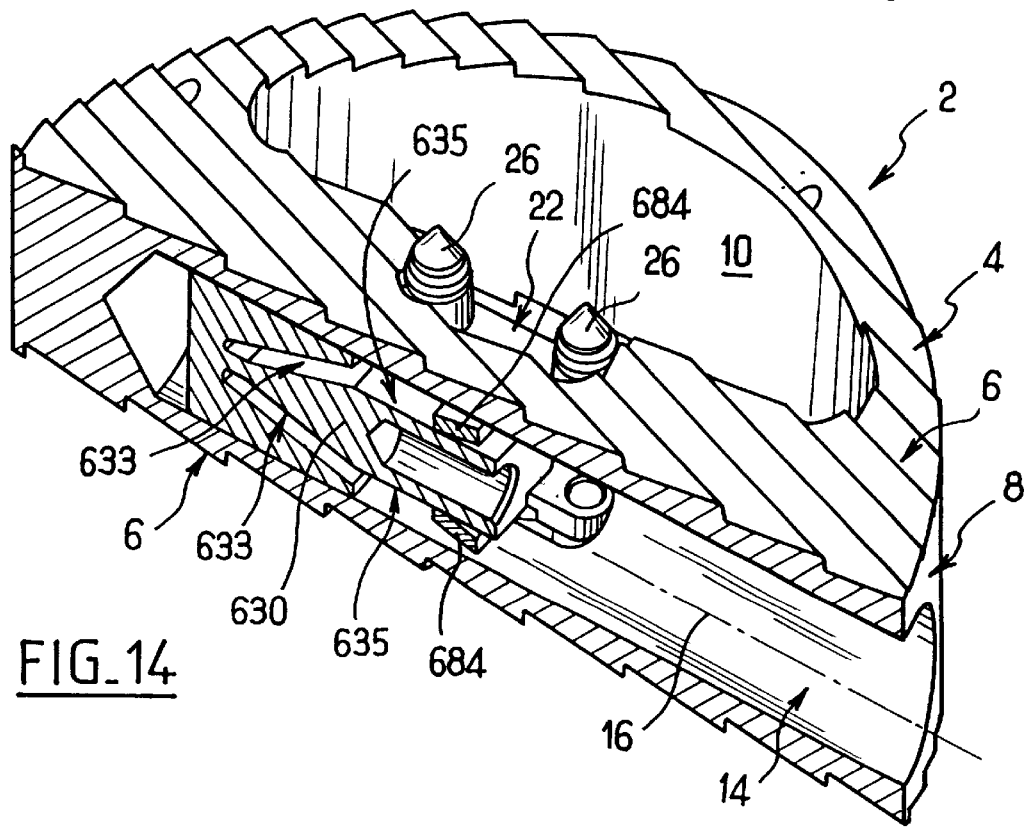
FIG_14

INTERSOMATIC SPINE IMPLANT HAVING ANCHORING ELEMENTS

BACKGROUND OF THE INVENTION

The invention relates to intersomatic spine implants.

Document FR-2 727 003 discloses an intersomatic spine implant for putting into the place of a vertebral disk after it has been removed, and comprising a body having two plane faces that come into contact with the adjacent vertebral bodies. It has two housings for receiving anchoring screws, disposed in such a manner that the screws project from respective contact faces so as to be anchored into the adjacent vertebral bodies. Each screw slopes relative to the associated contact face because the head of the screw projects from a side of the body so as to be capable of being driven once the implant has been received between the vertebral bodies. Nevertheless, it is difficult to put the screws into place because of the slope of their axes. Furthermore, the positioning of the screws cannot be improved in order to optimize the quality of the anchoring they provide without making them less accessible.

U.S. Pat. No. 5,702,391 discloses an intersomatic implant comprising a body, slidably movable pins in the body for projecting from outside faces of the body, and spherical cams slidably movable in an axial duct of the body. An actuator piece disposed at the mouth of the duct enables thrust to be applied to the cams which move the pins by a ramp effect so that they project and thus anchor the implant in the plates of the associated vertebrae. Such an implant makes it much easier to achieve robust anchoring between the vertebrae. However, the implant is very difficult to remove should that be necessary, which in contrast is not the case with the implant disclosed in above-mentioned FR-2 727 003 since it needs only to have the screws undone to eliminate anchoring between the implant and the plates.

SUMMARY OF THE INVENTION

An object of the invention is to provide an implant that is easy to install and remove.

To achieve this object, the invention provides an intersomatic spine implant comprising a body, at least one anchoring element movable relative to the body to project from a contact face of the body making contact with a vertebra, and at least one cam slidable relative to the body and suitable for displacing the anchoring element relative to the body by the effect of a ramp engaging the anchoring element, wherein the cam and the anchoring element are arranged so that the cam moves the anchoring element in two opposite displacement directions.

Thus, the anchoring element is moved by means of the cam, by taking action on the cam. Since action is no longer taken directly on the anchoring element, constraints associated with accessibility of the anchoring element are to a very large extent eliminated. As a result, the anchoring element is easier to drive into place during surgery. Furthermore, since it is no longer necessary to make the anchoring element directly accessible, its positioning can be modified in a very wide variety of ways so as to ensure that it performs its anchoring function as well as possible. Consequently, the operation of installing the anchoring element is made easier, while also making it possible to improve the quality of anchoring.

In addition, since the action of the cam is reversible, it enables the or each anchor element to be actuated so as to go from the extended position to the retracted position. It is then easy to remove the implant. This action of the cam on the anchoring element is positive in the sense that the cam entrains the anchoring element. The action of the cam does not consist solely in leaving the way open for the implant to be capable of penetrating into the body under the effect of external pressure exerted on the anchoring element by the material of the vertebrae. Thus, in particular, it is possible to remove the implant a long time after it has been put into place.

The implant of the invention may also present one or more of the following characteristics:

- the cam has a thread suitable for co-operating by screw engagement with an actuator for driving the cam from outside the body;
- the actuator is suitable for being mounted to move in rotation relative to the body;
- the cam is mounted to move sliding relative to the body;
- the cam has an end providing a face that is undercut relative to a travel direction of the cam so as to enable the cam to be extracted from the body;
- the implant includes at least two anchoring elements and at least two cams suitable for moving respective anchoring elements;
- the two cams are arranged so that their threads cooperate with a common actuator;
- the anchoring element slopes relative to a general plane of the contact face;
- the implant includes at least two anchoring elements suitable for projecting from the same contact face;
- the implant includes at least four anchoring elements suitable for projecting from the same contact face and disposed in two rows defining mutually-parallel alignment directions;
- the body has two contact faces for making contact with respective vertebrae and at least one recess extending between the contact faces;
- the portion of the anchoring element suitable for projecting from the contact face has faces that are undercut relative to the sliding direction of the element towards the vertebra; and
- the implant presents at least two anchoring elements and an element-carrier rigidly connected to the anchoring elements.

BRIEF DESCRIPTION OF THE DRAWINGS

Other characteristics and advantages of the invention appear further from the following description of five preferred embodiments given as non-limiting examples. In the accompanying drawings:

FIGS. 1 and 2 are two perspective views of an implant constituting a first embodiment of the invention shown respectively in the assembled state and in an exploded state;

FIGS. 3 and 4 are two section views of the FIG. 1 implant during two respective steps of installation thereof;

FIG. 5 is a view analogous to FIG. 4 showing the implant between two vertebrae;

FIGS. 6 and 7 are respectively an exploded perspective view and a section view of an implant constituting a second embodiment of the invention;

FIGS. 10 and 11 are perspective views showing an implant constituting a fourth embodiment of the invention respectively in the assembled state and in an exploded state;

FIG. 12 is a fragmentary axial section view of the cam and the screw of FIG. 11;

FIG. 13 is a perspective of an implant showing a fifth embodiment of the invention;

FIG. 14 is a section view of the implant on plane XIV—XIV of FIG. 13;

DESCRIPTION OF THE PREFERRED EMBODIMENTS

Figure 8:
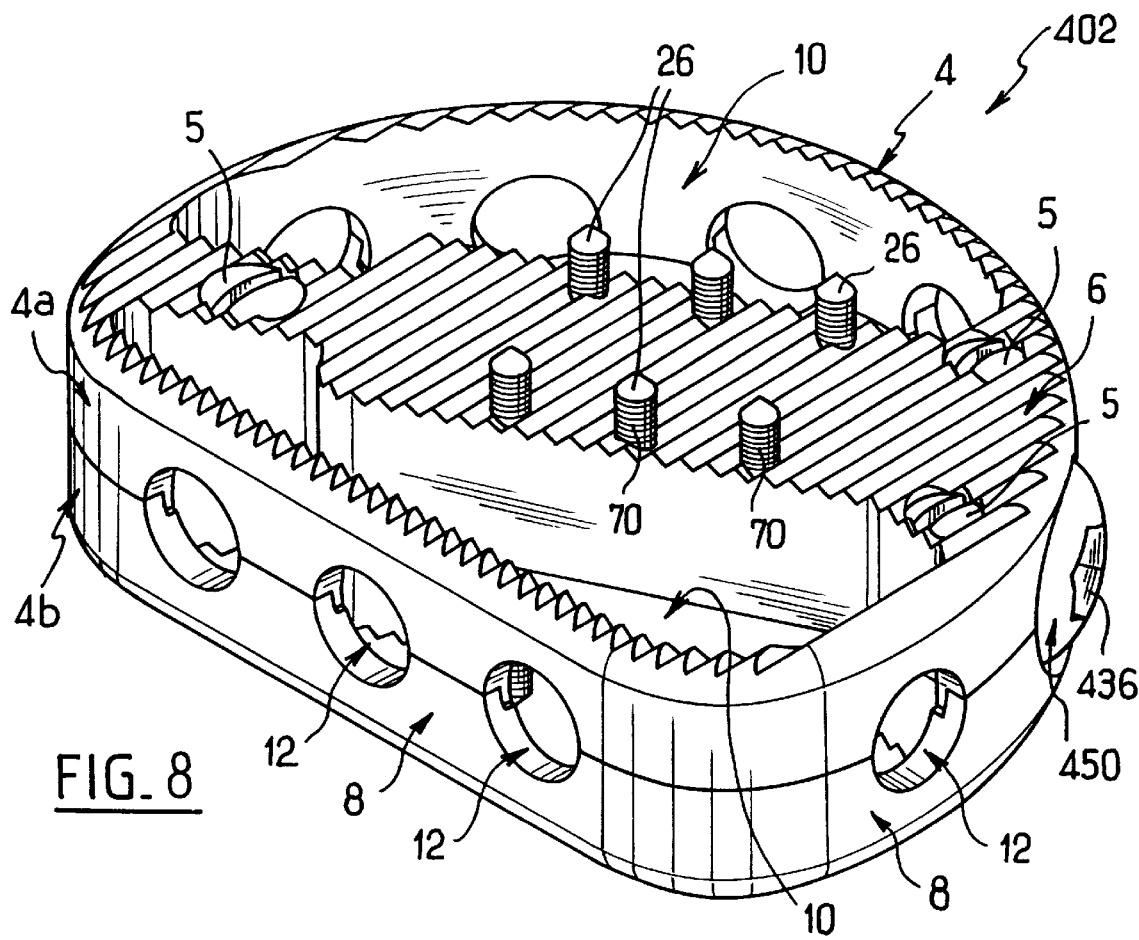
FIG. 8 is a perspective view of an implant constituting a third embodiment of the invention.

A first embodiment of the implant is described with reference to FIGS. 1 to 5. The implant 102 comprises a body 4 that is generally in the form of a rectangular parallelepiped flattened in one direction so as to define two large faces 6, namely a top face and a bottom face, and four side faces 8. The edges and the corners of the body are rounded to avoid injuring the tissues of the human body for which the implant is intended. The top and bottom faces 6 are generally plane in shape and they have respective transverse profiles that are sawtoothed or zigzag, the tips of the teeth defining continuous mutually-parallel edges. These edges provide good engagement of the top and bottom faces 6 against the plates of the vertebral bodies of the destination vertebrae 9, as shown in FIG. 5.

The body 4 has two through recesses 10 extending close to two opposite edges of the body and between the top and bottom faces 6 so as to open out into both of them. Furthermore, each side face 8 has an orifice 12 opening out into one of the recesses 10 halfway between the top and bottom faces 6. When the implant is put into place, the recesses 10 are filled with graft tissue which can thus grow towards the vertebral plates through the recesses 10 and the orifices 12.

The body 4 has a cylindrical duct 14 so that its axis 16 extends through two opposite corners of the body that are remote from the recesses 10, and parallel to the general planes of the top and bottom faces 6. The duct 14 is open at both ends. In the vicinity of a distal one of its ends, it presents a segment 18 of smaller diameter that is threaded. The remainder of the duct 14 constitutes a smooth segment 20 of larger diameter than the segment 18.

The body 4 has channels 22 of cylindrical shape extending from the segment 20 to the top and bottom faces 6. All of the channels 22 have axes 24 which intersect the axis 16 in the segment 20, in this case at right angles. There are twelve such channels 22 in this case. They are subdivided into two groups of six channels 22. In each group, the six channels 22 are parallel to one another, in axial alignment in pairs, and situated in a common plane that includes the axis 16. The section of FIGS. 3 and 4 lies in one such plane so that all six channels in one of the groups can be seen in these figures. This plane slopes relative to the general planes of the top and bottom faces 6 such that the axes 24 of the channels 22 slope likewise. The slopes are symmetrical and have the same angle for both groups of channels. In each group of six channels 22, three of the channels open out into the top face 6 and three into the bottom face 6. Each channel 22 that opens out into the top face 6 is in axial alignment with one of the channels in the same group that opens out into the bottom face. In each group, the three channels that open out into the same face are spaced apart a common pitch. Thus, in each face 6, channels 22 open out that are distributed in two rows defining mutually-parallel alignment directions, with the channels in each row sloping in opposite directions.

Each channel 22 slidably receives an anchoring element constituted in this case by a pin 26 having a smooth cylindrical body presenting a point at an end closer to the face 6 and presenting, at an opposite end, a head having a convex spherical face of radius greater than the radius of the channel 22 and of width greater than the diameter of the associated channel 22. The head is situated in the segment 20 and thus holds the pin 26 prisoner against being extended fully through the associated face 6.

The implant has a cam 130 that is circularly cylindrical about an axis lying on the axis 16. At a distal axial end it presents a threaded cylindrical face 134 suitable for entering into screw engagement with the segment 18 of the body. At a proximal axial end 136 it presents a head of diameter greater than the diameter of the segment 20 of the body so as to come into abutment against the outside of the body. The head presents a socket, e.g. a hexagonal socket with six flats, thus enabling the cam 130 to be rotated about its axis by means of a suitable tool such as a key.

Between its two ends, the cam 130 presents three broad cylindrical faces 138, three cylindrical faces 140 that are narrow compared with the broad faces 138, and three frustoconical faces 142 that slope towards the threaded distal end 134. These faces alternate and are distributed in three consecutive groups each comprising in the proximal-distal direction: a broad face 138; a frustoconical face 142; and a narrow face 140, the frustoconical face 142 providing a transition in level between the other two faces. The lengths of the faces along the axis 16 are identical for each type of face. These lengths are adapted so that when the threaded distal end 134 of the cam engages with only the proximal end of the segment 18, as shown in FIG. 3, the heads of the pins 26 bear against the narrow faces 140, with each narrow face 140 being in contact with the heads of four pins 26 whose axes 24 are coplanar in a plane perpendicular to the axis 16, whereas when the head of the cam 130 is in abutment against the body, as shown in FIG. 4, the heads of the pins 26 bear against the broad faces 138, with each broad face 138 being in contact with the four above-mentioned pins 26. The diameter of the narrow faces 140 is such that when in the position shown in FIG. 3, referred to below as the "retracted position", the points of the pins 26 do not project beyond the associated face 6, or project so little that they do not significantly impede installation of the implant 102 between the vertebral bodies. The diameter of the broad faces 138 is such that when in the position of FIG. 4, referred to below as the "extended position", the pins 26 project from the face 6, e.g. by one-fourth to one-third of their length, and penetrate far enough into the associated vertebral body to prevent the implant being withdrawn.

The implant is put into place as follows. After a vertebral disk has been removed, and after the recesses 10 have been filled with graft tissue, as mentioned above, the implant 102 is inserted between the vertebral bodies of the vertebrae 9 associated with the disk that has been removed. The height of the body 4 of the implant corresponds to the thickness of the removed disk. The implant is inserted in such a manner that the threaded segment 18 is substantially in the posterior position. The faces 6 extend facing respective vertebral plates, being parallel thereto and in contact therewith. The implant is inserted while it is in its retracted configuration as shown in FIG. 3.

Once the implant is in position, a key is used to drive the head of the cam 130 which is situated in the anterior position so as to cause the cam to turn about its axis 16. Given the screw engagement between the distal end 134 of the cam and the segment 18, the cam thus follows a helical path along its axis 16. For each group of four pins, the contiguous frustoconical face 142 comes progressively into contact with the heads of the pins and constitutes a ramp which, given its displacement towards the segment 18, urges the four pins so as to cause them to slide towards the outside of the body. As the pins 26 extend outwards, they penetrate into the vertebral plates and anchor the implant in the vertebrae. The four pins 26 then come to bear against the contiguous broad face 138 and project from the respective faces 6 in the extended configuration. At the end of driving the cam 130, the head of the cam bears against the body and the distal end 134 of the cam is at the distal end of the segment 18.

In a variant of this first embodiment, the screw engagement between the cam 130 and the body 4 could be replaced by snap-fastening or clipping to prevent the cam from moving relative to the body after the cam has merely been thrust parallel to its axis. The cam is then slidably movable relative to the body. Under such circumstances, its cross-section relative to its axis need not be circular, for example it could be rectangular.

A second embodiment of the implant is described with reference to FIGS. 6 and 7. Elements that differ from those of the first embodiment are given numerical references plus 100.

In the implant 202, the body 4 has substantially the same configuration as in the preceding embodiment, apart from the fact that the smooth larger-diameter segment 20 constitutes the entire length of the cam duct 14. In this case, the cam 130 is replaced by a set of three cams 230 and a screw 250. The screw 250 has a drive head 236 forming an abutment against the body, analogous to that of the cam 130. The screw has a threaded rod 252.

The three cams 230 are identical to one another. Each cam 230 is generally cylindrical in shape. It has a threaded cylindrical duct 253 suitable for co-operating with the rod 252 by screw engagement. Each cam 230 has four slots 254 each associated with a respective specific one of four pins 26 to be actuated by the cam. Each slot 254 extends in a plane that is radial relative to the axis 16 of the cam. Each slot 254 has a shallow, high portion 238, a low portion 240 which is deep relative to the shallow portion, and an intermediate portion 242 forming a transition in level between the high and low portions. The high portions of the four slots 254 in any one cam are contiguous to the proximal end of the cam. Perpendicularly to the axis 16, each slot has a profile in the form of an outwardly open circular arc extending over more than a semicircle, of radius that is constant along the slot, with the edges of the circular arc extending outwards level with the intermediate and low portions in the form of two mutually-parallel plane flanks. Each slot is adapted to receive the head of the associated pin 26 in the axial direction via either end, while preventing the head from escaping in the radial direction of the cam. The bottom of each slot 254 constitutes a first ramp for causing the associated pin 26 to slide outwards when the cam slides towards the distal end of the duct 14. An advantage of this embodiment is that it is reversible. Since the head of each pin 26 is held captive in the associated slot 254, the edges of the slot constitute a second ramp enabling the pin to be moved back into the retracted position when the cam 254 slides towards the proximal end of the duct.

The various parts of the implant are assembled as follows. After the pins 26 have been received in their channels 22 in the body 4, one of the cams 230 is slid to the central position associated with the pins 26 in the middle of the row. To be able to do this, the cam 230 must be capable of "getting past" the four pins 26 at one of the ends of the rows, e.g. the four pins 26 at the distal end if the cam is inserted via said end. This step is performed by inserting the cam 232 in the distal end of the duct 14 and inserting the pins 26 into respective slots 254. Since the pins 26 are initially projecting, continued thrust of the cam towards the center of the duct has the effect, given the ramps in the slots, of moving the pins 26 into the retracted configuration. As the cam continues to be thrust in, the distal ends of the pins leave the low portions 240 of the slots. Applying continued thrust to the cams serves to insert the pins in the centers of the rows into the high portions 238 of the slots 254 and finally to bring them into the low portions 240 of the cam. Thereafter, the cam 230 for occupying the distal position is inserted in the same manner. After that the cam 230 for occupying the proximal position is inserted in the same manner via the proximal end. Once all of the pins 26 are in the low portions 240 of the slots, in the retracted configuration, the screw 250 is screwed into the cam 230 so as to be in screw engagement therewith.

Once the implant has been installed between the vertebrae, the screw 250 is pushed towards the distal end of the duct 14, thereby causing the cams 230 to slide in the same direction. By means of the ramps at the bottoms of the slots 254, the pins are then caused to slide along their respective channels so as to move from the low portions 240 to the high portions and thus reach the extended position. Given the above-described reversibility, it is possible by means of steps that are the converse of those implemented for assembly, to remove the implant from its position between the vertebrae.

Figure 9:
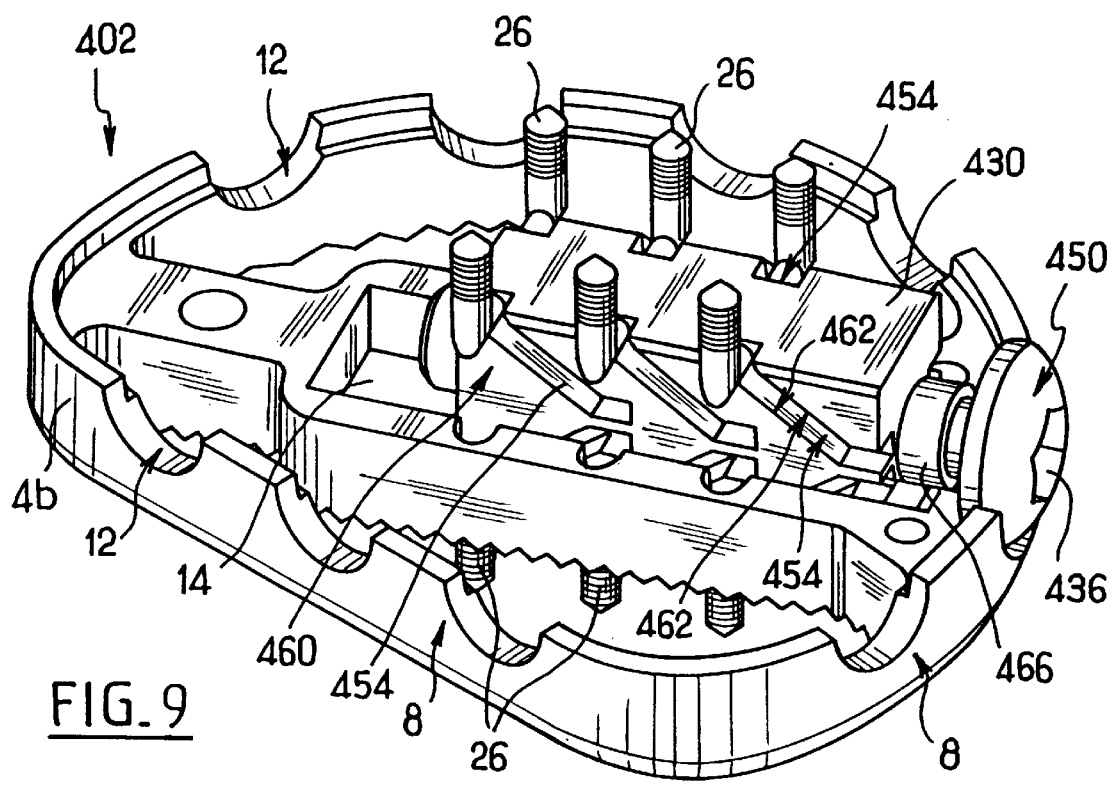
FIG. 9 is a perspective view of the FIG. 8 implant with the top portion of its body removed.

In the third embodiment, as shown in FIGS. 8 and 9 in which some of the numerical references have 400 added thereto, the body 4 in plane view generally has the shape of half a disk, being defined by a plane side wall 8 for occupying the posterior position and a circular side wall 8 for occupying an anterior position. Each side wall 8 has orifices 12 opening out into the recesses 10 as described above. In this case, the body 4 comprises a top portion 4a and a bottom portion 4b which meet in a joint plane parallel to the top and bottom faces 6, with each portion carrying one of said faces 6 and being fixed to the other by means of screws 5. There are still twelve channels 22, but they are oriented so that their axes are perpendicular to the top and bottom faces 6.

The cam duct 14 has a section that is generally rectangular in shape perpendicularly to its axis 16 and half of it is defined in each of the portions 4a and 4b of the body. The cam 430 has a male rectangular section corresponding to the female rectangular section of the duct 14 which receives it. It is suitable for sliding along its axis. The cam is generally in the form of a rectangular parallelepiped. The two longitudinal side faces 460 of the cam 430 have six slots 454 each suitable for receiving respective specific pins 26. To this end, instead of having a head, each pin has a respective projection that is received in the slot so that each pin is generally L-shaped, with the projections extending towards the other row of pins. Each slot 454 presents two mutually-parallel plane ramps or faces 462 that are perpendicular to the associated side face 460, and that slope relative to the sliding direction in such a manner that the end of the slot 454 that is further away from the associated face 6 is its end which is further away from the proximal end of the cam.

The cam 430 presents a threaded bore passing through it along its axis. The implant 402 has a screw 450 presenting a threaded rod suitable for screw co-operation with the cam 430. The screw 450 has a groove receiving a collar 466 that is secured to the body 450 that the screw 450 is free to rotate in the body while the cam 430 is free to slide in the body.

After the implant 402 has been inserted between the vertebrae 9 with the pins 26 in the retracted position, when the head 436 of the screw is driven, rotation of the screw causes the cam 430 to slide towards the distal end of the duct 14, which end is closed in this case, and by the effect of the ramps in the faces 462 of the slots oriented towards the associated faces 6, the pins 26 are caused to slide so as to project and take up the extended position.

The operation of the implant 402 is reversible, with the faces 462 of the slots that face away from the associated faces 6 being suitable for moving the pins 26 into the retracted position when the cam 430 slides towards the proximal end of the duct 14. Specifically, the proximal end associated with the head of the screw 436 opens out into the left-hand portion of the curved side wall 8. The pins 26 in this case present circumferential grooves 70 in the vicinity of their points on the segments thereof that are designed to project, with the grooves presenting respective faces that are undercut relative to the direction in which the pins slide so as to project, and the grooves improve anchoring of the pins by enabling bone growth to take place in the grooves.

Figure 11:
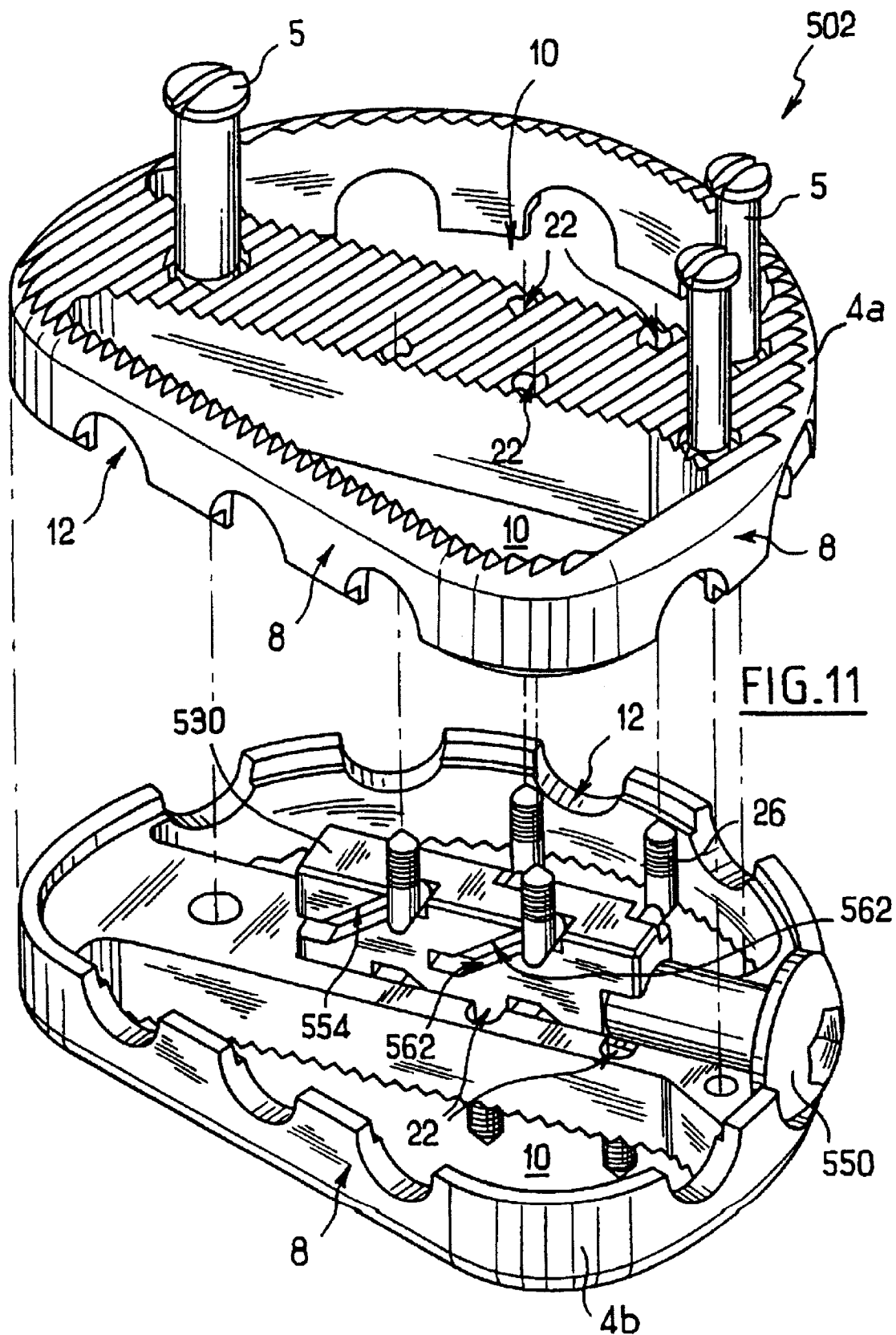

FIGS. 10 and 11 show a fourth embodiment with some of the reference numerals having 400 added thereto. In this case there are four pins 26 in each face 6 and they are oriented in the same manner as in the third embodiment. The slots 562 are analogous to those of the third embodiment but they are oriented in the opposite direction so that sliding the cam 530 towards the distal end of the cam duct 14 causes the pins 26 to project. The implant 502 has a screw 550 in screw engagement with the body 4 on the axis of the cam duct and suitable for urging the cam 530 at its proximal end in its duct towards the distal end of the duct.

With reference to FIG. 12, the proximal end of the cam has a cutout 572 suitable for slidably receiving the end of the screw 550 so that it can bear against the cam 530. Between the far wall of the cutout and its edge, the cam 530 presents a slot 574 with a flank 576 that presents an undercut relative to the cam sliding towards the proximal end of the duct. By way of example, this face 576 can be an annular plane perpendicular to the axis 16 of the cam and facing away from the proximal end.

In order to remove the implant, the screw 550 is removed and then a tool is inserted into the duct 14 that is suitable for bearing against the undercut face 576 as to catch hold of it and pull the cam towards the proximal end of the duct, thereby causing the pins 26 to be moved into the retracted configuration. This embodiment avoids the need to provide a threaded bore passing through the cam 530. It thus enables the dimensions of the cam 530 to be reduced and the dimensions of the recesses 10 for receiving graft tissue to be increased.

A fifth embodiment of the implant is described with reference to FIGS. 13 to 17. The implant 602 comprises a body 4 whose plane is general in the shape of a bean whose hilum is in the posterior position, the body being flat in one direction so as to define two large faces 6, namely a top face and a bottom face, and a peripheral side wall 8. The top and bottom faces 6 are generally plane in shape with a transverse profile that is sawtoothed or zigzag, the tips of the teeth defining mutually-parallel continuous edges. These teeth provide good engagement between the top and bottom faces 6 and the plates of the vertebral bodies of the vertebrae constituting the destination location.

The body 4 has two through recesses 10 extending between the top and bottom faces 6 and opening out into them. When the implant is put into place, the recesses 10 are filled with graft tissue which can thus grow towards the vertebral plates through the recesses 10.

The body 4 has a cylindrical duct 14 whose axis 16 extends between the recesses 10 parallel to the general planes of the top and bottom faces 6 and is separated from the single plane portion of the side face 8 by one of the recesses 10. The duct 14 opens out at only one of its ends.

The body 4 has two channels 22 opening out into each of the top and bottom faces. Each channel 22 is of constant section along an axis perpendicular to the main faces and in section its profile is rectangular with rounded ends. Each channel opens out on one side over its entire height into a respective one of the recesses 10 with which it is contiguous. Furthermore, it opens out sideways on its opposite side in its middle portion into the duct 14. The two channels 22 extend in register with each other on either side of the duct 14. The channels 22 thus put the two recesses 10 into communication with the duct 14.

In the vicinity of each of the main faces, each channel 22 receives a pair of anchoring elements each in the form of a pin 26 having a smooth cylindrical body presenting a point at its end closer to the face 6. Each pin 26 extends against a respective curved edge of the channel so as to slide there against perpendicularly to the main face 6 of the body.

Figure 15:
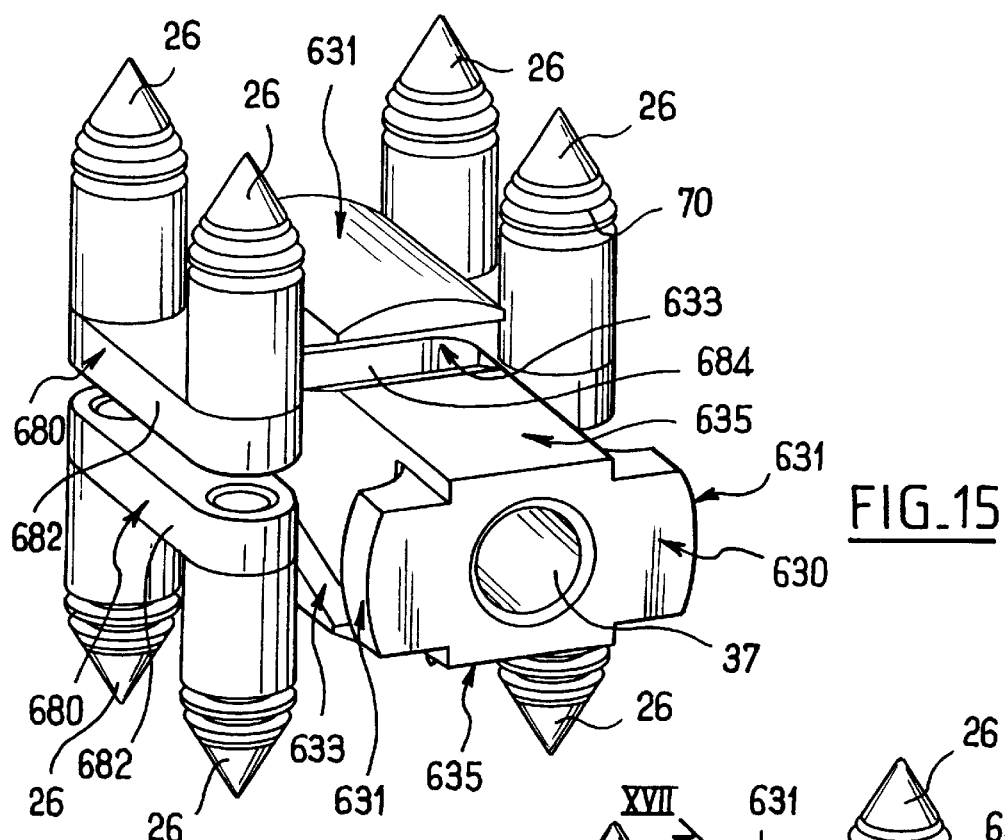
FIGS. 15 and 16 are two perspective views of the cam and the element-carrier of the FIG. 13 implant shown respectively in an element-retracted position and an element-extended position.
Figure 16:
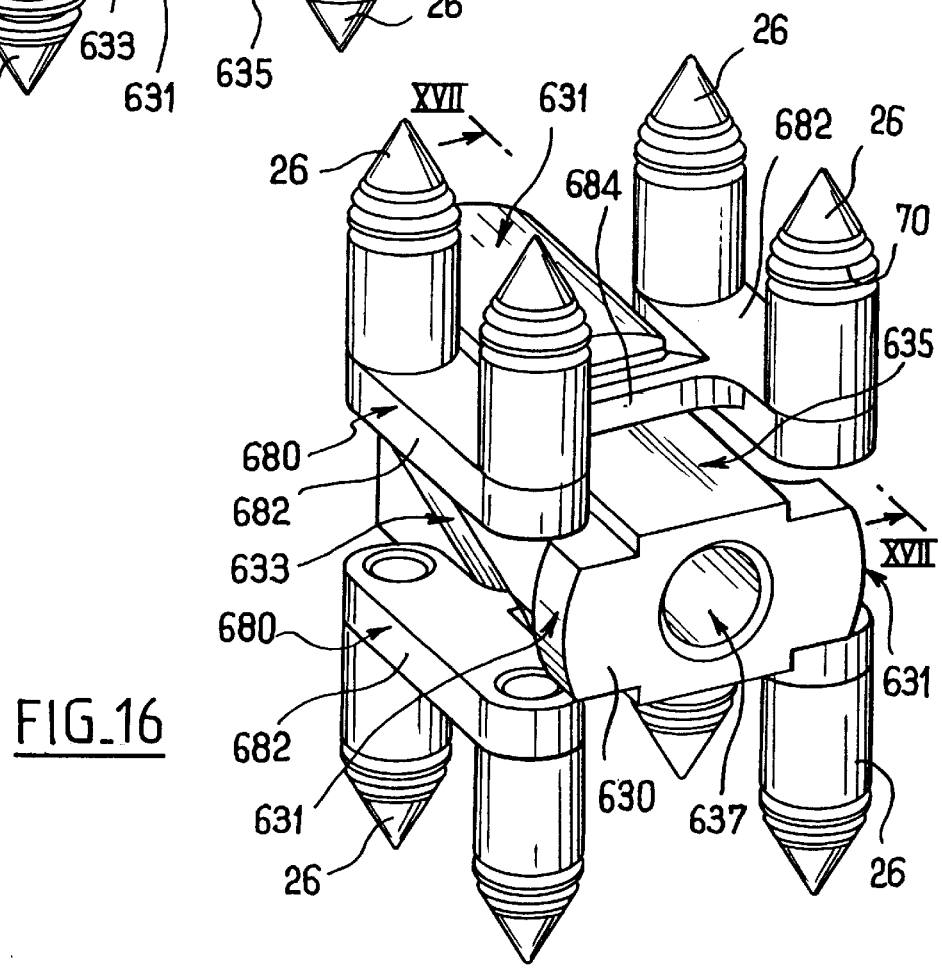
Figure 17:
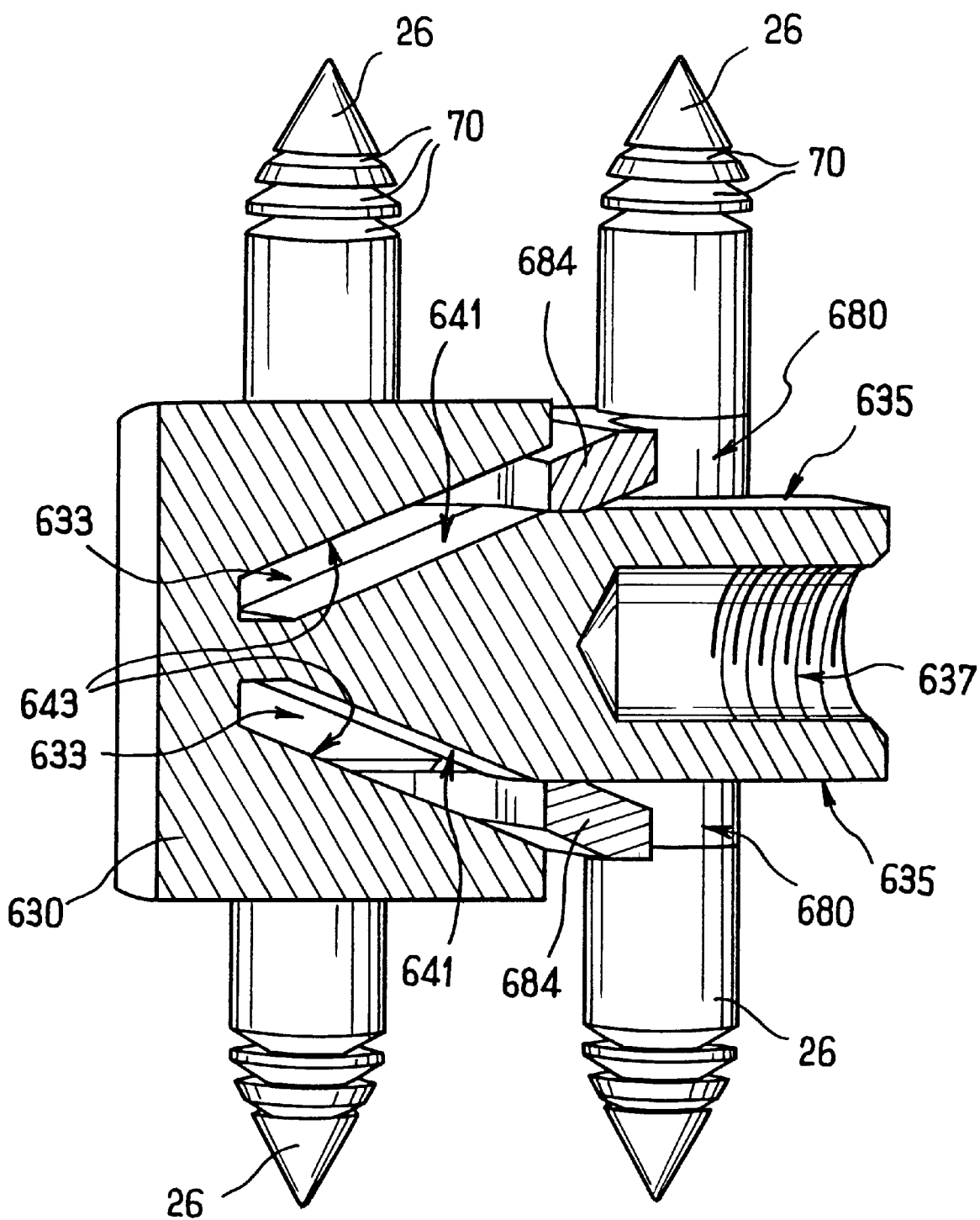
FIG. 17 is a section view of the cam and the element-carriers on the midplane XVII—XVII FIG. 16.

The implant includes two pin-carriers or anchoring element-carriers 680 associated with respective main faces 6. Each pin-carrier 680 is generally in the form of a flat H-shape having two rectangular branches 682 parallel to each other and a middle segment 684 interconnecting the middles of the branches. Each pin-carrier 680 has rigidly fixed thereon all four pins 26 associated with the corresponding main face 6. The bases of the four pins 26 rest on respective ends of the branches 682, and all lie on the same side of the pin-carrier. The two pin-carriers 680 extend permanently in register with each other so that their outlines coincide, and regardless of whether the pins 26 are in the extended or retracted position, as shown in FIGS. 15 and 16. The branches 682 extend in respective channels 22 and have the same profile, while the middle segment 684 extends across the duct 14.

The implant has a cam 630 with left and right cylindrical faces 631 that are left and right at the rear, and top and bottom at the front, for the purpose of slidably guiding the cam in the cylindrical duct 14. The "rear" of the cam is its end closest to the mouth of the duct 14. For each pin-carrier 680, the cam 630 has a corresponding slideway 633 and bearing surface 635 that can be seen in particular in FIGS. 14 and 17. The slideway 633 is formed by a very flat duct open to both longitudinal edges and sloping relative to the axis 16, going towards the corresponding main face when going from the front end towards the middle of the cam. The slideway 633 is closed at its front end and open at its rear end, with the inner face 641 of the slideway extending continuously from the bearing surface 635. This surface is parallel to the axis 16 and to the associated main face 6. The middle segment 684 can be moved by thrust against the slideway 633 and the bearing surface 635 as explained below. The sloping slideways 633 and the parallel bearing surfaces 635 give the cam a shape reminiscent of a boat anchor.

At its rear end, the cam has a tapped bore 637 whose thread can mesh with that of a suitable tool for driving the cam by pushing it or pulling it.

The implant is used as follows, with the pins 26 initially being in the retracted position as shown in FIG. 15. After a vertebral disk has been removed and after the recesses 10 have been filled with graft tissue as described above, the implant 2 is inserted between the vertebral bodies of the vertebrae associated with the disk that has been removed. The height of the body 4 of the implant corresponds substantially to the thickness of the removed disk. The faces 6 extend in register with the respective vertebral plates, parallel thereto, and in contact therewith. The cam is close to the mouth of the duct 14, at the rear.

The tool is screwed into the bore 637 of the cam and the cam 630 is pushed forwards. The ramp acting on each middle segment 684 via the inner face 641 of the associated slideway 633 causes the pin-carrier 680 together with the four pins 26 to move perpendicularly to the main face 6.

After the pins 26 have been caused to project from the main face 6, continued thrust on the cam causes the middle segment 684 to bear against the bearing surface 635 as shown in FIG. 14, thus locking the pins 26 in the extended position where the anchor in the vertebral plates. The tool is then unscrewed so as to be separated from the cam.

However, if it is desired to remove the implant, the tool is reconnected in the bore 637 of the cam via the duct 14 and then the cam is pulled so as to slide rearwards. The middle segment 684 then follows the bearing surface 635 and, by ramp engagement against the outer face 643 of the slideway 633, it becomes moved towards the axis 16 towards the inside of the implant, thereby retracting the pins 26 so that they no longer project. The cam thus enables the pins 26 to be driven in both directions, i.e. reversibly.

By having all four pins 26 in each group fixed together, it is possible to obtain very accurate guidance for the pins in the channels 22 without needing to provide a cylindrical channel for each pin. In addition, this guidance is obtained using a single two-part ramp surface 641, 635, or 643 for all four pins in any one given displacement direction.

At the base of the point forming its tip, each pin 26 has circular grooves 70 forming undercut zones and improving the anchoring of the pin in the vertebral plate.

The body 4 is made up of two portions that are assembled together on a joint plane (not shown) parallel to the main faces 6 and including the axis 16, thereby enabling the cam 630 and the pin-carriers 680 to be inserted in the body.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. An intersomatic spine implant comprising:
   a body having at least one anchoring element movable relative to the body to project from top and bottom contact faces of the body for contacting a vertebra; and
   at least one cam slidable relative to the body for displacing the anchoring element relative to the body through the faces by the effect of a ramp engaging the anchoring element,
   the cam and the anchoring element arranged so that the cam forcibly extends and retracts the anchoring element relative to the body,
   the cam having an element thereon for engaging the anchoring element to forcibly retract the anchoring element from the vertebra,
   the anchoring element having an enlarged portion for engaging said element on said cam, and
   the retraction element on said cam being a slot adapted to receive said enlarged portion of said anchoring element, wherein said slot extends radially outwardly relative to said cam axis, each slot having a first and second portion radially displaced from said cam axis wherein said first portion is at a distance which causes said anchoring element to move into engagement with said vertebra and said second portion is at a distance which causes said anchoring element to move out of engagement with said vertebra.

2. The implant according to claim 1 wherein the cam includes an actuator and has a thread suitable for co-operating by screw engagement with the actuator for driving the cam from outside the body.

3. The implant according to claim 1 wherein the cam is slidably mounted relative to the body.

4. The implant according to claim 1 wherein at least two anchoring elements are included and at least two cams are included suitable for moving respective anchoring elements.

5. The implant according to claim 4 wherein the at least two cams co-operate with a common actuator on the implant.

6. The implant according to claim 1 wherein the anchoring element slopes relative to a general plane of the contact face.

7. The implant according to claim 1 wherein at least two anchoring elements are included each projecting from the same contact face.

8. The implant according to claim 1 wherein at least four anchoring elements projecting from the same contact face are included and disposed in two rows defining mutually-parallel alignment directions.

9. The implant according to claim 1 wherein the body has two contact faces for making contact with respective vertebrae and at least one recess extending between the contact faces.

10. A spinal implant comprising:
    a body having an internal opening therein and first and second external faces for contacting first and second vertebra respectively, said faces each having at least one channel therethrough;
    a projection element slideable through each of said at least one channel with respect to said body extending beyond the first and second faces of said body adapted for engagement with said first and second vertebrae; and
    a cam received within said internal opening for acting on said projection element to selectively move said projection element into and out of engagement with said vertebra, said cam having a retraction element thereon for engaging said projection element to retract said projection element from said vertebra,
    said projection element having an enlarged portion for engaging said retraction element on said cam, and
    said retraction element on said cam having a slot adapted to receive said enlarged portion of said projection element, wherein said slot extends radially outwardly relative to said cam axis, each slot having a first and second portion radially displaced from said cam axis wherein said first portion is at a distance which causes said projection element to move into engagement with said vertebra and said second portion is at a distance which causes said projection element to move out of engagement with said vertebra.

11. The implant as set forth in claim 10 wherein said first and second faces are generally planar and said projection element moves in a direction generally perpendicular thereto.

12. The implant as set forth in claim 10 wherein selective movement of the cam within said internal opening acts on an internal end of said projection element to move an external end into and out of engagement with said vertebrae.

13. The implant as set forth in claim 12 wherein the internal opening is an axial bore.

14. The implant as set forth in claim 13 wherein the selective movement of the cam is in direction along a longitudinal axis of said bore.

15. The implant as set forth in claim 14 wherein said cam includes a ramped groove which captures said internal end of said projection.

16. The spinal implant as set forth in claim 14 wherein a plurality of projection elements are provided in said body and extending through said first and second faces thereof and said cam includes a ramped groove capturing said internal end of each of said projection elements.

17. The spinal implant as set forth in claim 10 wherein said cam has a driver portion located outside of said body.

18. The implant according to claim 10 wherein at least two projection elements are included and at least two cam surfaces are included, each surface suitable for moving a respective one of said at least two projection elements.

19. The implant according to claim 18 wherein the at least two cam surfaces co-operate with a common actuator on the implant.

20. The implant according to claim 10 wherein at least two projection elements are included each projecting from either said first external face or said second external face.

21. The implant according to claim 10 wherein at least four anchoring elements projecting from either said first external face or said second external face are included and disposed in two rows defining mutually-parallel alignment directions.

* * * * *

UNITED STATES PATENT AND TRADEMARK OFFICE
CERTIFICATE OF CORRECTION

PATENT NO.    : 6,527,803 B1
DATED         : March 4, 2003
INVENTOR(S)   : Yves Crozet It is certified that error appears in the above-identified patent and that said Letters Patent is hereby corrected as shown below:

<u>Title page,</u>
Item [75], Inventors, "route" should read -- Route --.
Item [73], Assignee, "Dimso" should read -- DIMSO --.

Signed and Sealed this

Sixth Day of May, 2003

JAMES E. ROGAN
*Director of the United States Patent and Trademark Office*